United States Patent
Shen et al.

(10) Patent No.: US 12,344,620 B2
(45) Date of Patent: Jul. 1, 2025

(54) BRD4 INHIBITOR COMPOUND IN SOLID FORM AND PREPARATION METHOD THEREFOR AND USE THEREOF

(71) Applicant: CSPC ZHONGQI PHARMACEUTICAL TECHNOLOGY (SHIJIAZHUANG) CO., LTD., Shijiazhuang (CN)

(72) Inventors: Chunli Shen, Shanghai (CN); Yong Liu, Shanghai (CN); Huanyu Bian, Shanghai (CN); Chengde Wu, Shanghai (CN); Jiahu Wu, Shanghai (CN)

(73) Assignee: CSPC ZHONGQI PHARMACEUTICAL TECHNOLOGY (SHIJIAZHUANG) CO., LTD., Shijiazhuang (CN)

( * ) Notice: Subject to any disclaimer, the term of this patent is extended or adjusted under 35 U.S.C. 154(b) by 913 days.

(21) Appl. No.: 17/593,668

(22) PCT Filed: Mar. 23, 2020

(86) PCT No.: PCT/CN2020/080741
§ 371 (c)(1),
(2) Date: Sep. 22, 2021

(87) PCT Pub. No.: WO2020/192637
PCT Pub. Date: Oct. 1, 2020

(65) Prior Publication Data
US 2022/0185820 A1    Jun. 16, 2022

(30) Foreign Application Priority Data
Mar. 22, 2019   (CN) .......................... 201910225039.6

(51) Int. Cl.
*C07D 495/14*        (2006.01)
(52) U.S. Cl.
CPC ........ *C07D 495/14* (2013.01); *C07B 2200/13* (2013.01)
(58) Field of Classification Search
CPC .................................................. C07D 495/14
See application file for complete search history.

(56) References Cited

U.S. PATENT DOCUMENTS

| | | |
|---|---|---|
| 5,712,274 A | 1/1998 | Sueoka et al. |
| 8,476,260 B2 | 7/2013 | Miyoshi et al. |
| 9,125,915 B2 | 9/2015 | Miyoshi et al. |
| 11,312,726 B2 | 4/2022 | Shen et al. |
| 2014/0213575 A1 | 7/2014 | Schmees et al. |

FOREIGN PATENT DOCUMENTS

| | | |
|---|---|---|
| CN | 101910182 A | 12/2010 |
| EP | 2239264 A1 | 10/2010 |
| JP | 2014-525421 A | 9/2014 |
| WO | 2009084693 A1 | 7/2009 |
| WO | WO 2015/018520 A1 | 2/2015 |
| WO | WO 2017/030814 A1 | 2/2017 |
| WO | WO 2017/223268 A1 | 12/2017 |
| WO | WO 2019/056950 A1 * | 3/2019 |

* cited by examiner

*Primary Examiner* — Shawquia Jackson
(74) *Attorney, Agent, or Firm* — Hoxie & Associates LLC

(57) ABSTRACT

Disclosed are a solid form and a crystal form of a compound represented by formula (I) used as a BRD4 inhibitor, a preparation method therefor, and an application thereof in the preparation of a medicine for treating BRD4-related diseases. (I).

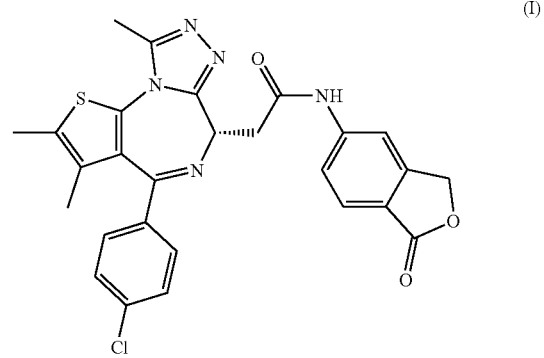

15 Claims, 3 Drawing Sheets

BRD4 INHIBITOR COMPOUND IN SOLID FORM AND PREPARATION METHOD THEREFOR AND USE THEREOF

CROSS-REFERENCE TO RELATED APPLICATIONS

This application is a U.S. National Stage Application under 35 U.S.C. § 371 of International Application No. PCT/CN2020/080741, which was filed on Mar. 23, 2020, which claims the benefit of and priority to Chinese Patent Application No. 201910225039.6, filed on Mar. 22, 2019, each of which are incorporated herein by reference in their entireties.

TECHNICAL FIELD

The present disclosure relates to solid forms and crystal forms of a compound of formula (I) as a small molecule BRD4 inhibitor, and the preparation method therefor, and relates to their use in the manufacture of a medicament for treating BRD4-related diseases.

BACKGROUND

Histone acetylation can regulate gene transcription and chromosome structure, plays an important role in epigenetics. As a "reader" of histone acetylation recognition gene, BET (bromodomain and extra-terminal domain) protein can specifically bind to acetylated lysine residues and recruit other transcription factors. By participating in protein-protein interactions, a mediator complex is formed to phosphorylate RNA polymerase, which activates gene transcription and regulates c-Myc and other downstream genes. Cancer cell proliferation is highly dependent on specific genes (e.g., c-Myc), and enhancement of expression of the specific genes plays an important role in cancer cell proliferation. Studies have shown that tumor cells are overly dependent on specific genes, making them very sensitive to BET inhibitors. The presence of BET inhibitors prevents the BET proteins from binding to histone acetylated lysine, thereby blocking expression of Myc by transcription factors, so as to inhibit tumor growth.

The BET protein family comprises 4 members: BRD2, BRD3, BRD4 and BRDT, each member comprising two N-terminal tandems (BD1 and BD2), an extra-terminal domain (ET), several conserved regions (A, B, SEED regions) and a C-terminal motif (CTM). Among them, BRD4 is the most extensively studied member, and it has been found that the occurrence of hematologic tumors including lymphomas (e.g., acute myelolymphoma, etc.), leukemias (e.g., acute lymphoblastic leukemia, etc.), myelomas (e.g., multiple myelomas, etc.) and solid tumors such as neurocytoma, gliomas, breast cancers (e.g., triple negative breast cancer, etc.), gastrointestinal tumors (e.g., colorectal cancer, etc.), and prostate cancers etc., are all related with the overexpression of BRD4, but no drug targeting BRD4 has been approved on the market up to now.

SUMMARY OF THE DISCLOSURE

In one aspect, the present disclosure provides a compound of formula (I) in solid form,

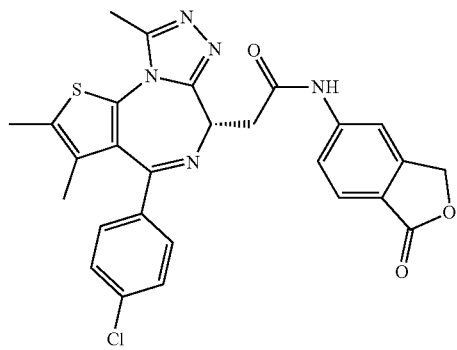

In some embodiments of the present disclosure, the solid is in crystal form.

In some embodiments of the present disclosure, the crystal form is a crystalline form A of the compound of formula (I) having an X-ray powder diffraction pattern comprising characteristic diffraction peaks at the following 2θ angles: 7.03±0.2°, 11.28±0.2°, 14.00±0.2°.

In some embodiments of the present disclosure, the crystalline form A has an X-ray powder diffraction pattern comprising characteristic diffraction peaks at the following 2θ angles: 7.03±0.2°, 11.28±0.2°, 20.07±0.2°.

In some embodiments of the present disclosure, the crystalline form A has an X-ray powder diffraction pattern comprising characteristic diffraction peaks at the following 2θ angles: 7.03±0.2°, 19.48±0.2°, 20.07±0.2°, 26.05±0.2°.

In some embodiments of the present disclosure, the crystalline form A has an X-ray powder diffraction pattern comprising characteristic diffraction peaks at the following 2θ angles: 7.03±0.2°, 11.28±0.2°, 17.31±0.2°, 19.48±0.2°, 20.07±0.2°, 26.05±0.2°.

In some embodiments of the present disclosure, the crystalline form A has an X-ray powder diffraction pattern comprising characteristic diffraction peaks at the following 2θ angles: 7.03±0.2°, 11.28±0.2°, 14.00±0.2°, 15.11±0.2°, 17.31±0.2°, 19.48±0.2°, 20.07±0.2°, 22.86±0.2°.

In some embodiments of the present disclosure, the crystalline form A has an X-ray powder diffraction pattern comprising characteristic diffraction peaks at the following 2θ angles: 7.03±0.2°, 11.28±0.2°, 14.00±0.2°, 15.11±0.2°, 17.31±0.2°, 19.48±0.2°, 20.07±0.2°, 26.05±0.2°.

In some embodiments of the present disclosure, the crystalline form A has an X-ray powder diffraction pattern comprising characteristic diffraction peaks at the following 2θ angles: 7.03±0.2°, 11.28±0.2°, 12.39±0.2°, 14.00±0.2°, 15.11±0.2°, 17.31±0.2°, 19.48±0.2°, 20.07±0.2°, 22.86±0.2°, 26.05±0.2°.

In some embodiments of the present disclosure, the crystalline form A has an X-ray powder diffraction pattern comprising characteristic diffraction peaks at the following 2θ angles: 7.03±0.2°, 11.28±0.2°, 12.39±0.2°, 14.00±0.2°, 14.87±0.2°, 15.11±0.2°, 17.31±0.2°, 19.48±0.2°, 20.07±0.2°, 22.86±0.2°.

In some embodiments of the present disclosure, the crystalline form A has an X-ray powder diffraction pattern comprising characteristic diffraction peaks at the following 2θ angles: 7.03±0.2°, 11.28±0.2°, 12.39±0.2°, 14.00±0.2°, 14.87±0.2°, 15.11±0.2°, 17.31±0.2°, 19.48±0.2°, 20.07±0.2°, 22.86±0.2°, 26.05±0.2°.

In some embodiments of the present disclosure, the crystalline form A has an X-ray powder diffraction pattern comprising characteristic diffraction peaks at the following 2θ angles: 7.03±0.2°, 11.28±0.2°, 12.39±0.2°, 14.00±0.2°, 14.87±0.2°, 15.11±0.2°, 17.31±0.2°, 17.68±0.2°, 19.48±0.2°, 20.07±0.2°, 22.86±0.2°.

In some embodiments of the present disclosure, the crystalline form A has an X-ray powder diffraction pattern comprising characteristic diffraction peaks at the following 2θ angles: 7.03±0.2°, 11.28±0.2°, 12.39±0.2°, 14.00±0.2°, 14.87±0.2°, 15.11±0.2°, 17.31±0.2°, 17.68±0.2°, 19.48±0.2°, 20.07±0.2°, 22.86±0.2°, 26.05±0.2°.

In some embodiments of the present disclosure, the crystalline form A has an XRPD pattern substantially as shown in FIG. 1.

In some embodiments of the present disclosure, the XRPD pattern analysis data for the crystalline form A is as shown in Table 1:

TABLE 1

XRPD analysis data for the crystalline form A of the compound of formula (I)

| No. | 2θ angle (°) | Intensity (counts) | Relative intensity (%) |
|---|---|---|---|
| 1 | 7.034 | 3861 | 100 |
| 2 | 8.714 | 67 | 1.7 |
| 3 | 9.958 | 162 | 4.2 |
| 4 | 11.276 | 1594 | 41.3 |
| 5 | 12.386 | 458 | 11.9 |
| 6 | 13.310 | 208 | 5.4 |
| 7 | 14.004 | 816 | 21.1 |
| 8 | 14.866 | 385 | 10 |
| 9 | 15.106 | 739 | 19.1 |
| 10 | 17.314 | 1087 | 28.2 |
| 11 | 17.684 | 340 | 8.8 |
| 12 | 18.000 | 193 | 5 |
| 13 | 19.485 | 1570 | 40.7 |
| 14 | 20.073 | 1736 | 45 |
| 15 | 21.555 | 135 | 3.5 |
| 16 | 21.855 | 86 | 2.2 |
| 17 | 22.855 | 741 | 19.2 |
| 18 | 24.855 | 74 | 1.9 |
| 19 | 25.314 | 73 | 1.9 |
| 20 | 26.051 | 1250 | 32.4 |
| 21 | 27.175 | 193 | 5 |
| 22 | 27.609 | 295 | 7.6 |
| 23 | 28.479 | 203 | 5.3 |
| 24 | 29.091 | 111 | 2.9 |
| 25 | 29.564 | 207 | 5.4 |
| 26 | 30.234 | 234 | 6.1 |
| 27 | 31.458 | 121 | 3.1 |
| 28 | 31.987 | 84 | 2.2 |
| 29 | 32.524 | 88 | 2.3 |
| 30 | 33.486 | 78 | 2 |

In some embodiments of the present disclosure, the crystalline form A has a differential scanning calorimetry curve with an onset of an endothermic peak at 289.22±3° C.

In some embodiments of the present disclosure, the DSC curve of the crystalline form A is substantially as shown in FIG. 2.

In some embodiments of the present disclosure, weight loss of the crystalline form A in the thermal gravimetric analysis pattern is 1.626% at 300.00±3° C.

In some embodiments of the present disclosure, the TGA pattern of the crystalline form A is substantially as shown in FIG. 3.

In some embodiments of the present disclosure, the crystal form is a crystalline form B of the compound of formula (I) having an X-ray powder diffraction pattern comprising characteristic diffraction peaks at the following 2θ angles: 5.50±0.2°, 8.36±0.2°, 11.87±0.2°.

In some embodiments of the present disclosure, the crystalline form B has an X-ray powder diffraction pattern comprising characteristic diffraction peaks at the following 2θ angles: 5.50±0.2°, 8.36±0.2°, 12.66±0.2°.

In some embodiments of the present disclosure, the crystalline form B has an X-ray powder diffraction pattern comprising characteristic diffraction peaks at the following 2θ angles: 5.50±0.2°, 8.36±0.2°, 11.87±0.2°, 12.39±0.2°, 12.66±0.2°, 15.11±0.2°, 17.35±0.2°, 18.70±0.2°.

In some embodiments of the present disclosure, the crystalline form B has an XRPD pattern substantially as shown in FIG. 4.

In some embodiments of the present disclosure, the XRPD pattern analysis data for the crystalline form B is as shown in Table 2.

TABLE 2

XRPD analysis data for the crystalline form B of the compound of formula (I)

| No. | 2θ angle (°) | D-spacing (A) | Relative intensity (%) |
|---|---|---|---|
| 1 | 5.499 | 16.0587 | 100 |
| 2 | 6.804 | 12.9802 | 15.9 |
| 3 | 7.082 | 12.4717 | 17.4 |
| 4 | 8.363 | 10.5636 | 26.9 |
| 5 | 11.868 | 7.4504 | 21.6 |
| 6 | 12.386 | 7.1403 | 20.5 |
| 7 | 12.660 | 6.9865 | 34 |
| 8 | 15.106 | 5.8603 | 22.4 |
| 9 | 15.657 | 5.6553 | 16 |
| 10 | 15.713 | 5.6353 | 13.3 |
| 11 | 17.354 | 5.1059 | 26.2 |
| 12 | 18.695 | 4.7424 | 29.6 |
| 13 | 20.790 | 4.2691 | 15.3 |
| 14 | 21.221 | 4.1832 | 18.8 |
| 15 | 21.474 | 4.1346 | 15.6 |
| 16 | 22.559 | 3.9382 | 19.3 |
| 17 | 22.681 | 3.9172 | 20.1 |
| 18 | 23.072 | 3.8518 | 22.2 |
| 19 | 24.340 | 3.6539 | 15.1 |
| 20 | 26.283 | 3.388 | 13 |

In another aspect, the present disclosure also provides a preparation method of the compound of formula (I) in the solid form, wherein the solid form is the crystalline form A, comprising:
(1) adding the compound of formula (I) into a solvent to form a suspension or a solution;
(2) stirring the suspension or the solution in a constant-temperature thermomixer, then separating, and drying to obtain the crystalline form A of the compound of formula (I).

In some embodiments of the present disclosure, the separation in step (2) of the preparation method is centrifugation or filtration.

In some embodiments of the present disclosure, the separation in step (2) of the preparation method is centrifugation.

In some embodiments of the present disclosure, the solvent of the preparation method is a single solvent selected from the group consisting of $C_{1-4}$alkyl-O—$C_{1-4}$alkyl, $C_{1-4}$alkylC(=O)O$C_{1-4}$alkyl, $C_{1-4}$alkyl-CN, $C_{1-4}$alkyl-OH or $C_{1-4}$alkylC(=O)$C_{1-4}$alkyl.

In some embodiments of the present disclosure, the single solvent in the preparation method is methyl tert-butyl ether, ethyl acetate, acetonitrile, ethanol, acetone, methanol or methyl ethyl ketone.

In some embodiments of the present disclosure, the solvent in the preparation method is a mixed solvent of $C_{1-4}$alkylC(=O)$C_{1-4}$alkyl and water, or a mixed solvent of $C_{1-4}$alkyl-OH and water.

In some embodiments of the present disclosure, for the mixed solvent consisting of $C_{1-4}$alkylC(=O)$C_{1-4}$alkyl and water of the preparation method, the volume ratio of the $C_{1-4}$alkylC(=O)$C_{1-4}$alkyl and water is 1-5:1, preferably 2:1; or for the mixed solvent consisting of $C_{1-4}$alkyl-OH and water, the volume ratio of the $C_{1-4}$alkyl-OH and water is 1-5:1, preferably 3:1.

In some embodiments of the present disclosure, the mixed solvent of the preparation method is a mixed solvent of acetone and water, or a mixed solvent of ethanol and water.

In some embodiments of the present disclosure, the mixed solvent of the preparation method is a mixed solvent of acetone-water with a volume ratio of 2:1, or a mixed solvent of ethanol-water with a volume ratio of 3:1.

The term "$C_{1-4}$alkyl" refers to any straight or branched chain group containing 1 to 4 carbon atoms, such as methyl, ethyl, n-propyl, isopropyl, n-butyl, isobutyl, tert-butyl and the like. And each "$C_{1-4}$alkyl" may be the same or different.

In some embodiments of the present disclosure, the weight-volume ratio of the compound to the solvent in the preparation method is 1 g: 5-15 mL, or 1 g: 5-12 mL, or 1 g: 5-10 mL.

In some embodiments of the present disclosure, the stirring temperature of the preparation method is 25° C.-45° C.

In some embodiments of the present disclosure, the stirring time of the preparation method is 12 hours to 50 hours, or 12 hours to 48 hours, or 12 hours to 24 hours.

In another aspect, the present disclosure also provides a preparation method of the compound of formula (I) in the solid form, wherein the solid form is the crystalline form B, comprising:
(1) adding the compound of formula (I) into a solvent to form a suspension or a solution;
(2) stirring the suspension or the solution in a constant-temperature thermomixer, then separating, and drying to obtain the crystalline form B of the compound of formula (I).

In some embodiments of the present disclosure, the separation in step (2) of the preparation method is centrifugation or filtration.

In some embodiments of the present disclosure, the separation in step (2) of the preparation method is centrifugation.

In some embodiments of the present disclosure, the solvent of the preparation method is tetrahydrofuran.

In some embodiments of the present disclosure, the weight-volume ratio of the compound to the solvent of the preparation method is 1 g: 5-10 mL.

In some embodiments of the present disclosure, the stirring temperature of the preparation method is 25° C.-45° C.

In some embodiments of the present disclosure, the stirring time of the preparation method is 12 hours to 50 hours, or 12 hours to 48 hours, or 12 hours to 24 hours.

In another aspect, the present disclosure provides a pharmaceutical composition comprising, as described above, the compound of formula (I) in solid form or a crystal mixture of any two or more crystal forms.

In another aspect, the present disclosure also provides the use of the compound of formula (I) in solid form or the pharmaceutical composition described above in the manufacture of a medicament for treating BRD4-related diseases.

In some aspects of the present disclosure, the use is characterized in that the BRD4-related diseases include tumors.

In some embodiments of the present disclosure, the use is characterized in that the tumors include hematological tumors and advanced solid tumors, wherein the hematological tumors include leukemia, lymphoma and myeloma, and the advanced solid tumors include neurocytoma, glioma, breast cancer, gastrointestinal tumor and prostate cancer; preferably, the leukemia is acute lymphoblastic leukemia, or the lymphoma is acute myeloid lymphoma, or the breast cancer is triple negative breast cancer, or the gastrointestinal tumor is colorectal cancer.

In another aspect, the present disclosure also relates to the compound of formula (I) in solid form or the pharmaceutical composition described above for use in the treatment of BRD4-related diseases.

In some embodiments of the present disclosure, the solid form of a compound of formula (I) or the pharmaceutical composition described above, wherein the BRD4-related diseases include tumors.

In some embodiments of the present disclosure, the solid form of a compound of formula (I) or the pharmaceutical composition described above, wherein the tumors include hematological tumors and advanced solid tumors, wherein the hematological tumors include leukemia, lymphoma and myeloma, and the advanced solid tumors include neurocytoma, glioma, breast cancer, gastrointestinal tumor and prostate cancer; preferably, the leukemia is acute lymphoblastic leukemia, or the lymphoma is acute myeloid lymphoma, or the breast cancer is triple negative breast cancer, or the gastrointestinal tumor is colorectal cancer.

In another aspect, the present disclosure also relates to a method for treating a BRD4-related disease of a subject in need thereof, comprising administrating the compound of formula (I) in solid form or the pharmaceutical composition described above to the subject.

In some embodiments of the present disclosure, the method for treating a disease of a subject, wherein the disease includes tumors.

In some embodiments of the present disclosure, the method for treating a disease of a subject, wherein the tumors include hematological tumors and advanced solid tumors, wherein the hematological tumors include leukemia, lymphoma and myeloma, and the advanced solid tumors include neurocytoma, glioma, breast cancer, gastrointestinal tumor and prostate cancer; preferably, the leukemia is acute lymphoblastic leukemia, or the lymphoma is acute myeloid lymphoma, or the breast cancer is triple negative breast cancer, or the gastrointestinal tumor is colorectal cancer.

The "subject" includes all members of animals, including, but not limited to, mammals (e.g., mice, rats, felines, monkeys, canines, horses, pigs, etc.) and humans.

The term "substantially as shown in the FIGURE" means that at least 50%, or at least 60%, or at least 70%, or at least 80%, or at least 90%, or at least 95%, or at least 99% of the peaks in the X-ray powder diffraction pattern or DSC curve or TGA pattern are shown in the figure thereof.

DEFINITIONS AND DESCRIPTIONS

The following terms and phrases as used herein are intended to have the following meanings, unless otherwise indicated. A particular phrase or term should not be considered as indefinite or unclear without being specifically defined, but rather construed according to common meaning. When a brand name is used herein, it is intended to refer to its corresponding commercial product or its active ingredient.

The intermediate compounds of the present disclosure may be prepared by many synthetic methods well known to those skilled in the art, including the specific embodiments exemplified below, embodiments formed by combinations of them with other chemical synthetic methods, and equivalents thereof well known to those skilled in the art, and preferred embodiments include, but not limited to, the examples of the present disclosure.

The chemical reactions of the specific embodiments of the present disclosure are carried out in suitable solvents that are compatible with the chemical changes of the present disclosure and the reagents and materials required for the same. In order to obtain the compounds of the present disclosure, it is sometimes necessary for those skilled in the art to modify or select the synthesis steps or reaction schemes based on the existing embodiments.

The present disclosure will be specifically illustrated below by way of examples, which are not intended to limit the present disclosure in any way.

All solvents used in the present disclosure are commercially available and can be used without further purification.

The solvent used in the present disclosure can be obtained commercially. The present disclosure uses the following abbreviations: DCM represents dichloromethane; DMF represents N,N-dimethylformamide; DMSO represents dimethyl sulfoxide; EtOH represents ethanol; MeOH represents methanol; TFA represents trifluoroacetic acid; TsOH represents p-toluenesulfonic acid; mp represents melting point; $EtSO_3H$ represents ethanesulfonic acid; $MeSO_3H$ represents methanesulfonic acid; ATP represents adenosine triphosphate; HEPES represents 4-hydroxyethylpiperazine ethanesulfonic acid; EGTA represents ethylene glycol bis(2-aminoethylether)tetraacetic acid; $MgCl_2$ represents magnesium dichloride; $MnCl_2$ represents manganese dichloride; DTT represents dithiothreitol.

Technical Effects

The compound of the formula (I) described herein has good crystalline form stability and is easy to prepare medicaments; the crystalline forms of the present disclosure show excellent activity to BRD4, has better pharmacokinetic property and oral absorption rate, have the characteristics of high activity, good metabolic stability, good solubility, suitability for oral administration and the like, and can provide more effective treatment for diseases caused by abnormal expression of BRD4.

1.1 Powder X-Ray Diffraction (X-Ray Powder Diffractometer, XRPD)

Instrument model: Bruker D8 advanced X-ray diffractometer

Test method: approximately 10-20 mg of sample was used for XRPD detection.

The detailed XRPD parameters were as follows:

X-ray generator: Cu, kα, (λ=1.54056 Å).

Tube voltage: 40 kV, tube current: 40 mA.

Emission slit: 1 deg.

Height limiting slit: 10 mm

Scattering slit: 1 deg.

Receiving a slit: 0.15 mm

Monochromator: Fixed Monochromator

Scanning range: for the crystalline form A: 4-33 deg; and for the crystalline form B: 4-35 deg Scanning speed: 10 deg/min 1.2 Differential Scanning Calorimetry (Differential Scanning Calorimeter, DSC)

Instrument model: TA Q2000 differential scanning calorimeter

Test method: the sample (0.5-1 mg) was placed in DSC aluminum pot for testing, and the sample was heated from 30° C. to 300° C. under the condition of 50 mL/min $N_2$ at the heating rate of 10° C./min.

1.3 Thermal Gravimetric Analysis (Thermal Gravimetric Analyzer, TGA)

Instrument model: TA Q5000IR thermal gravimetric analyzer

Test method: the sample (2-5 mg) was placed in TGA platinum pan for testing, and the sample was heated from room temperature to weight loss of 20% under the condition of 25 mL/min $N_2$ at the heating rate of 10° C./min.

1.4 Dynamic Vapor Sorption (DVS) Analysis Method of the Present Disclosure

Instrument model: SMS DVS advantage dynamic vapor sorption analyzer

Testing conditions: the sample (10-20 mg) was placed in DVS sample trays for testing.

Detailed DVS Parameters:

Temperature: 25° C.

Balancing: dm/dt=0.01%/min (shortest: 10 min, longest: 180 min)

Drying: drying for 120 min at 0% RH

RH (%) testing step: 10%

RH (%) testing step range: 0%-90%-0%

The evaluation of hygroscopicity was classified as follows:

| Moisture absorption classification | ΔW % |
|---|---|
| Deliquescence | absorbing sufficient water to form liquid |
| Very hygroscopic | ΔW % ≥ 15% |
| Hygroscopic | 15% > ΔW % ≥ 2% |
| Slightly hygroscopic | 2% > ΔW % ≥ 0.2% |
| No or almost no hygroscopicity | ΔW % < 0.2% |

Note:
ΔW % represents the increase in weight by moisture sorption of the test sample at 25 ± 1° C. and 80 ± 2% RH.

SPECIFIC EMBODIMENTS

Figure 1:
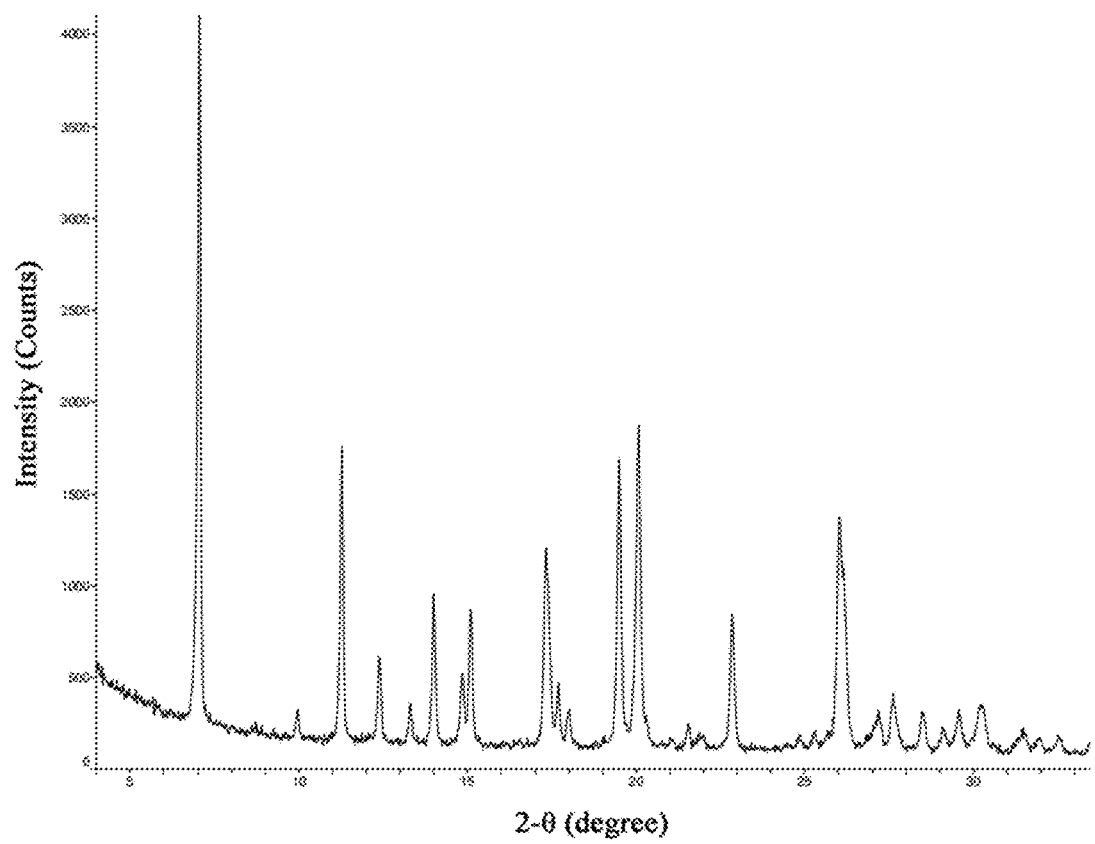
FIG. 1 is an XRPD pattern of Cu-Kα radiation of the crystalline form A of the compound of formula (I).

For better understanding of the present disclosure, the following illustration is made with reference to specific examples, but the present disclosure is not limited to the specific embodiments.

Example 1: The Preparation of the Compound of Formula (I)

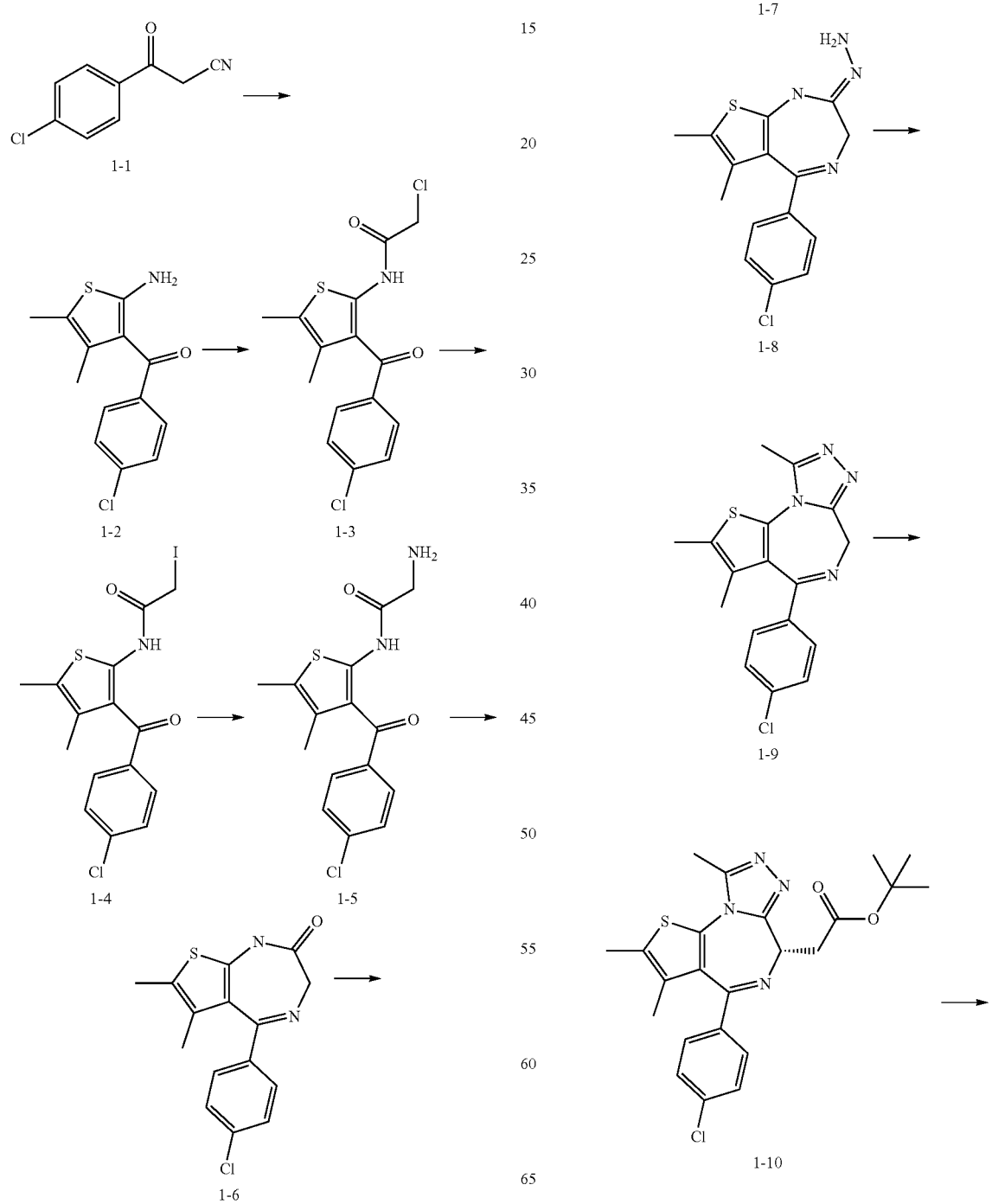

-continued

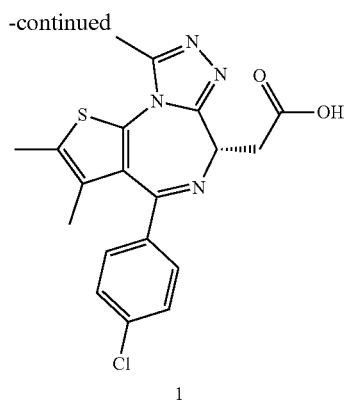

1

Step 1:

Compound 1-1 (25.00 g, 139.20 mmol, 1.00 eq), 2-butanone (11.04 g, 153.12 mmol, 13.63 mL, 1.10 eq) and morpholine (12.13 g, 139.20 mmol, 12.25 mL, 1.00 eq) were dissolved in ethanol (200.00 mL), followed by addition of sublimed sulphur (4.46 g, 139.20 mmol, 1.00 eq). The suspension was heated to 70° C. and stirred for 12 hours under nitrogen gas protection. The reaction was first evaporated under reduced pressure to give a yellow oil, to which water (500 mL) was added, and extracted with ethyl acetate (200 mL×4). The combined organic phases were collected, washed with saturated saline solution (200 mL), dried over anhydrous sodium sulfate, filtered and evaporated under reduced pressure. The crude was purified on silica gel column (petroleum ether/ethyl acetate=10/1) to give compound 1-2. $^1$H NMR (400 MHz, CDCl$_3$) δ ppm 7.47 (d, J=8.0 Hz, 2H), 7.38 (d, J=8.0 Hz, 2H), 6.43 (br s, 2H), 2.13 (s, 3H), 1.56 (s, 3H).

Step 2:

Compound 1-2 (10.00 g, 37.63 mmol, 1.00 eq) was dissolved in chloroform (100.00 mL), and 2-chloroacetyl chloride (6.37 g, 56.45 mmol, 4.49 mL, 1.50 eq) was added dropwise, after which the reaction was stirred at 70° C. for 1 h. The reaction mixture was washed with saturated sodium bicarbonate solution (100 mL) and saturated saline solution (50 mL), then dried over anhydrous sodium sulfate, filtered and evaporated under reduced pressure. The crude compound obtained was recrystallized from methanol (40 mL) to give compound 1-3. $^1$H NMR (400 MHz, CDCl$_3$) δ ppm 11.81 (br s, 1H), 7.58 (dd, J=2.0, 6.4 Hz, 2H), 7.45 (dd, J=2.2, 8.6 Hz, 2H), 4.25 (s, 2H), 2.29 (s, 3H), 1.72 (s, 3H).

Step 3:

Compound 1-3 (11.00 g, 32.14 mmol, 1.00 eq) and sodium iodide (9.63 g, 64.28 mmol, 2.00 eq) were added to tetrahydrofuran (50.00 mL), and the mixture was stirred at 60° C. for 2 h. The reaction was directly evaporated under reduced pressure to give compound 1-4, which was used directly in the next reaction without purification. LCMS (ESI) m/z: 433.9 (M+1).

Step 4:

Compound 1-4 (14.00 g, 32.28 mmol, 1.00 eq) was dissolved in tetrahydrofuran (100.00 mL), cooled to −60° C. and charge with ammonia gas for 30 minutes. The reaction mixture was slowly heated to 20° C. and stirred for 3 hours. The reaction was directly evaporated under reduced pressure. The resulting solid was dissolved in ethyl acetate (150 mL), washed with water (50 mL×3) and saturated saline solution (50 mL), dried over anhydrous sodium sulfate, filtered and then evaporated under reduced pressure to give compound 1-5 which was used directly in the next reaction. LCMS (ESI) m/z: 322.9 (M+1), 344.9 (M+Na).

Step 5:

Compound 1-5 (10.00 g, 30.98 mmol, 1.00 eq) was dissolved in isopropanol (150.00 mL) and glacial acetic acid (50.00 mL), and stirred at 90° C. for 3 h. The solvent was removed from reaction solution under reduced pressure. The remaining mixture was dissolved in chloroform (20 mL), washed with saturated sodium bicarbonate solution (20 mL) and saturated saline solution (20 ml), dried over anhydrous sodium sulfate, filtered and then evaporated under reduced pressure. The crude product was recrystallized from ethyl acetate (50 mL) to give compound 1-6. $^1$H NMR (400 MHz, CDCl$_3$) δ ppm 8.98 (br s, 1H), 7.46 (d, J=8.4 Hz, 2H), 7.35 (d, J=8.4 Hz, 2H), 4.80 (d, J=8.8 Hz, 1H), 3.93 (d, J=8.6 Hz, 1H), 2.28 (s, 3H), 1.59 (s, 3H).

Step 6:

Phosphorus pentasulfide (17.07 g, 76.79 mmol, 8.17 mL, 3.60 eq) was added to a continuously stirred suspension of sodium carbonate (4.07 g, 38.39 mmol, 1.80 eq) in 1,2-dichloroethane (200.00 mL), stirred at 20° C. for 1 hour, then compound 1-6 (6.50 g, 21.33 mmol, 1.00 eq) was added. The resulting suspension reacted at 65° C. for 5 hours. The reaction mixture was cooled to 20° C. and filtered, and the filter cake was dissolved in ethyl acetate (2 L) and washed with saturated saline solution (500 mL), dried over sodium sulfate, filtered and then evaporated under reduced pressure. The crude compound was purified on silica gel column (petroleum ether/ethyl acetate=5/1) to give compound 1-7.

Step 7:

To a suspension of compound 1-7 (3.50 g, 10.91 mmol, 1.00 eq) in methanol (5.00 mL) was added hydrazine hydrate (1.67 g, 32.72 mmol, 1.62 mL, 98% purity, 3.00 eq) at 0° C., and the reaction was stirred at 0° C. for 1 h. The reaction mixture was filtered, and the filter cake was oven-dried to obtain compound 1-8, which was used directly in the next reaction. LCMS (ESI) m/z: 318.9 (M+1).

Step 8:

To the mixture of compound 1-8 (2.50 g, 7.84 mmol, 1.00 eq) in toluene (100.00 mL) was added triethyl orthoacetate (3.82 g, 23.52 mmol, 4.29 mL, 3.00 eq). The reaction was stirred at 80° C. for 1 h. The reaction mixture was evaporated under reduced pressure directly and the crude compound was recrystallized from ethyl acetate (10 mL) to give compound 1-9. LCMS (ESI) m/z: 344.9 (M+1).

Step 9:

To a solution of compound 1-9 (1.50 g, 4.38 mmol, 1.00 eq) in tetrahydrofuran (180 mL) was added LiHMDS (1M, 8.76 mL, 2.00 eq) dropwise at −70° C. The reaction was stirred at this temperature for 1 hour, then a solution of tert-butyl 2-bromoacetate (1.28 g, 6.57 mmol, 970.82. µL, 1.50 eq) in tetrahydrofuran (20 mL) was added dropwise. After the addition was complete, the reaction was slowly heated to 20° C. and stirred for 5 hours. The reaction mixture was quenched with saturated NH$_4$Cl solution (50 mL), extracted with ethyl acetate (100 mL), washed with saturated saline solution (50 mL), dried over anhydrous sodium sulfate, filtered and then evaporated under reduced pressure. The crude compound was purified by flash column chromatography and the resulting compound was separated by SFC to give compound 1-10 (basic-EtOH, column: AS (250 mm×30 mm, 5 µm), mobile phase B: 30%, flow rate (mL/min): 55) ([α]$^{25}_D$+54 (C 0.6, CHCl$_3$)). LCMS (ESI) m/z: 457.0 (M+1).

Step 10:

Compound 1-10 (150.00 mg, 328.23 μmol, 1.00 eq) were dissolved in dichloromethane (5.00 mL) and trifluoroacetic acid (1.00 mL) and the reaction was stirred for 4 h at 20° C. The reaction mixture was directly evaporated under reduced pressure to give compound 1, which was used directly in the next reaction. LCMS (ESI) m/z: 401.0 (M+1).

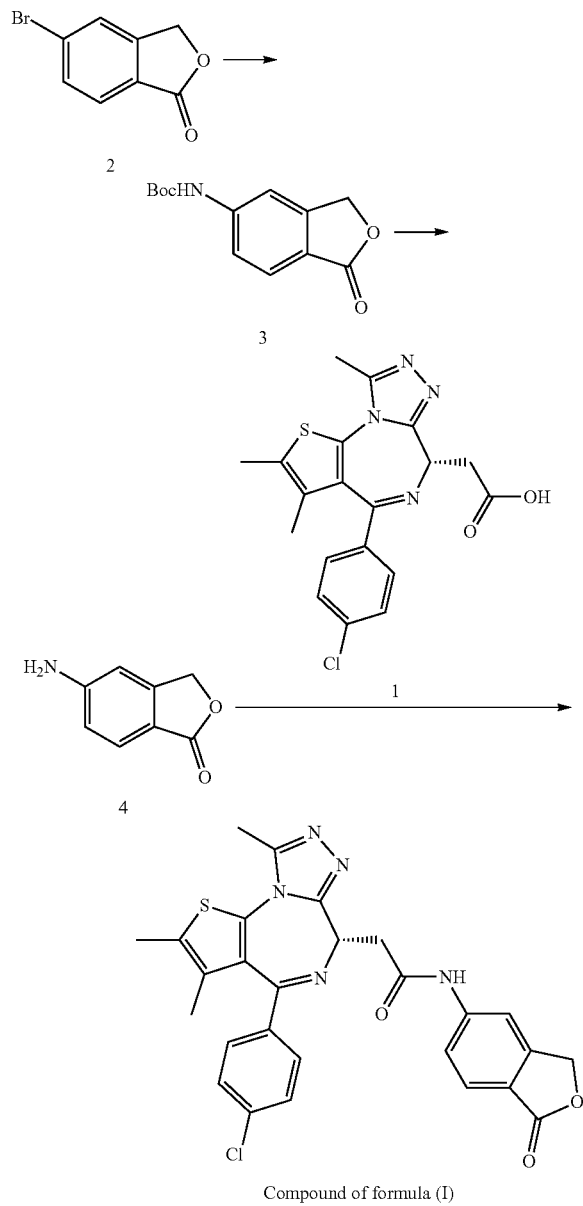

Step 11:

Compound 2 (0.78 g, 3.66 mmol, 1 eq), tert-butyl carbamate (643.39 mg, 5.49 mmol, 1.5 eq), tris(dibenzylideneacetone) dipalladium (335.29 mg, 366.15. μmol, 0.1 eq), cesium carbonate (2.39 g, 7.32 mmol, 2 eq) and 4,5-bis (diphenylphosphino)-9,9-dimethylxanthene (211.86 mg, 366.15. μmol, 0.1 eq) were added to 1,4-dioxane (10 mL) and reacted at 100° C. for 12 hours under nitrogen gas protection. To the reaction mixture was added water (20 mL), ethyl acetate (20 mL) was added, insoluble matter was filtered off by filtration, the aqueous phase was extracted with ethyl acetate (10 mL), and the combined organic phases were dried over anhydrous sodium sulfate, filtered and evaporated under reduced pressure. Purification was performed using a flash column apparatus to give compound 3. LCMS (ESI) m/z: 250.1 (M+1).

Step 12:

Trifluoroacetic acid (3.85 g, 33.77 mmol, 2.5 mL, 18.30 eq) was added to compound 3 (0.46 g, 1.85 mmol, 1 eq) in anhydrous dichloromethane (20 mL) and reacted at 20° C. for 12 hours after addition. The reaction was washed with water (20 mL), the pH of the aqueous phase was adjusted to 7 with saturated sodium bicarbonate solution, the aqueous phase was extracted with dichloromethane (10 mL×2), the combined organic phases were dried over anhydrous sodium sulphate, filtered and evaporated under reduced pressure. Compound 4 was obtained and used in the next reaction without further purification. LCMS (ESI) m/z: 149.8 (M+1).

Step 13:

$POCl_3$ (76.50 mg, 498.90 μmol, 46.36 μL, 2 eq) was added to a solution of compound 1 (100 mg, 249.45 μmol, 1 eq) and compound 4 (44.65 mg, 299.34 μmol, 1.2 eq) in pyridine (2 mL) at 0° C., after addition the temperature was raised to 20° C. for 1.5 hours. The reaction was quenched by the addition of water (3 ml), and the pH of the aqueous phase was adjusted to 7 with 2N hydrochloric acid. The aqueous phase was extracted with dichloromethane (5 mL×3), and the organic phase was dried over anhydrous sodium sulfate, filtered and evaporated under reduced pressure. Purification by Thin Layer Chromatography (dichloromethane/methanol=10/1) gave the compound of formula (I) as a glass paste or foam adhering to the vial wall. LCMS (ESI) m/z: 532.1 (M+1). $^1$H NMR (400 MHz, $CDCl_3$) δ ppm 9.98 (br s, 1H), 7.94 (d, J=6.8 Hz, 1H), 7.67 (d, J=8.0 Hz, 1H), 7.32-7.36 (m, 3H), 7.24-7.27 (m, 2H), 5.08-5.16 (m, 2H), 4.57-4.61 (m, 1H), 3.78-3.84 (m, 1H), 3.45-3.50 (m, 1H), 2.63 (s, 3H), 2.36 (s, 3H), 1.63 (s, 3H).

Example 2: Preparation of the Crystalline Form a of the Compound of Formula (I)

About 50 mg of the compound of formula (I) was weighed and added into a 1.5 mL glass vials, respectively, and an appropriate amount of solvents (see Table 3) was added until a suspension was formed, which was sealed with a sealing film, and stirred in constant-temperature thermomixer at 40° C. for 48 hours. Samples were then centrifuged in a centrifuge, and the centrifuged solid was added into a vacuum oven for drying overnight at 30° C. to obtain the crystalline form A of the compound of formula (I).

TABLE 3

Crystalline form screening experiment with different solvents

| No. | Solvent | Solvent amount (mL) | Crystalline form (XRPD) |
|---|---|---|---|
| 1 | acetone:water (2:1) | 0.3 | A |
| 2 | methyl tert-butyl ether | 0.5 | A |
| 3 | ethyl acetate | 0.5 | A |
| 4 | acetonitrile | 0.5 | A |
| 5 | ethanol | 0.5 | A |
| 6 | acetone | 0.4 | A |
| 7 | methanol | 0.6 | A |
| 8 | methyl ethyl ketone | 0.4 | A |
| 9 | ethanol:water (3:1) | 0.4 | A |

Example 3: Preparation of the Crystalline Form B of the Compound of Formula (I)

About 50 mg of the compound of formula (I) was weighed and added into a 1.5 mL glass vial, and tetrahydrofuran (0.2 mL) was added until a suspension was formed, which was sealed with a sealing film. The mixture was stirred in constant-temperature thermomixer at 40° C. for 48 hours. Samples were then centrifuged in a centrifuge, and the centrifuged solid was added into vacuum oven for drying overnight at 30° C. to obtain the crystalline form B of the compound of formula (I).

Experimental Example 1: Solid Stability Test of the Crystalline Form a of the Compound of Formula (I)

According to guidelines on stability test of API and formulations (The general guidelines of the Chinese Pharmacopoeia 2015 edition volume IV 9001), the stability of the crystalline form A of the compound of formula (I) was investigated under accelerated (40° C./75% RH, sealed) and prolonged (25° C./60% RH, sealed) conditions.

1.5 g of the crystalline form A of the compound of formula (I) was weighed, placed on the bottom of a glass bottle for sample and spread it to a thin layer, respectively, wherein the samples to be tested under 25° C./60% RH and 40° C./75% RH conditions were packed in double-layer LDPE (low-density polyethylene) bags. Each layer of LDPE bags were sealed separately, and then the LDPE bag was put into an aluminum foil bag and heat-sealed. The samples placed under different conditions were sampled and detected on the 90th day, the detection result was compared with the initial detection result on the 0th day, and the test results were shown in the following table 4:

TABLE 4

Solid stability test results for the crystalline form A of the compound of formula (I)

| Test conditions | Time point | Appearance | Crystalline form (XRPD) | Content (%) | Total impurity (%) |
|---|---|---|---|---|---|
| — Powder | 0 day | White Powder | Crystalline form A | 98.7 | 0.17 |
| 40° C./75% RH, sealed | 90 days | White Powder | Crystalline form A | 99.2 | 0.19 |
| 25° C./60% RH, sealed | 90 days | White Powder | Crystalline form A | 99.4 | 0.12 |

"RH": Relative humidity.

Conclusion: the crystalline form A of the compound of formula (I) has good stability.

Experimental Example 2: Hygroscopicity Study of the Crystalline Form A of the Compound of Formula (I)

Experiment Materials

SMS DVS advantage dynamic vapor sorption analyzer

Experiment Method 10-15 mg of the crystalline form A of the compound of formula (I) was placed on a DVS sample tray for testing.

Experiment Results

Figure 5:
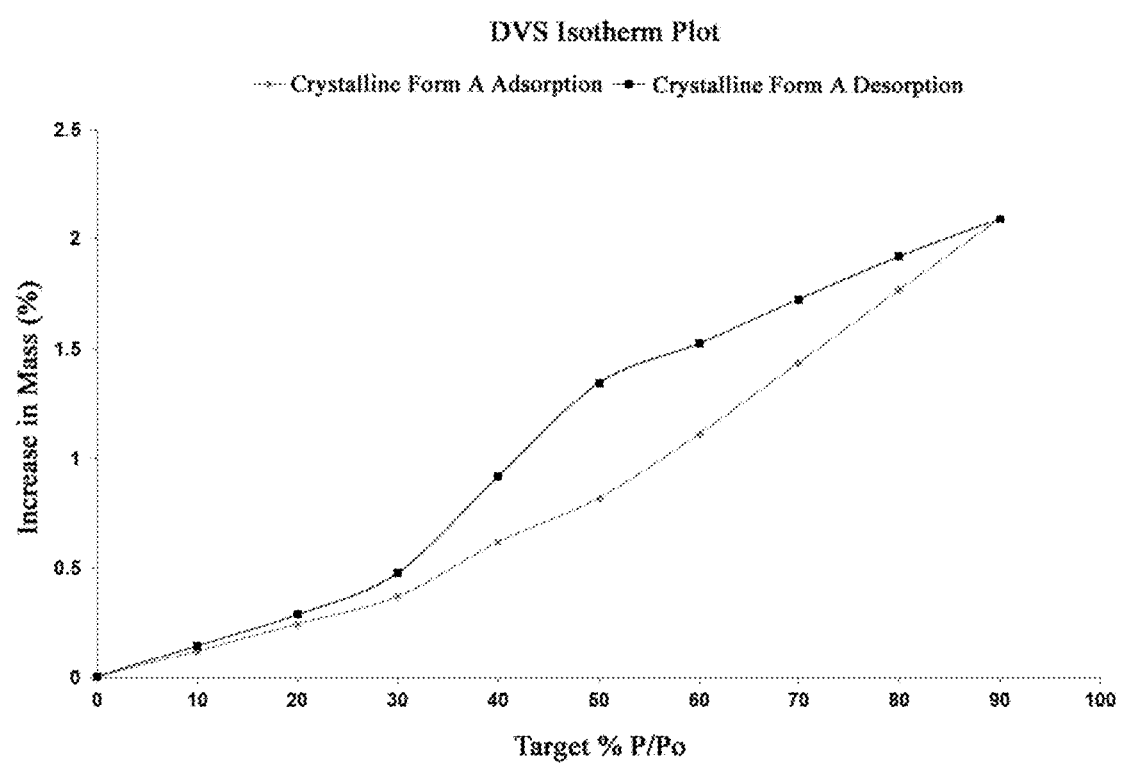
FIG. 5 is a DVS isotherm of the crystalline form A of the compound of the compound of formula (I).

The DVS pattern of the crystalline form A of the compound of formula (I) is shown as FIG. 5, ΔW=1.789%.

Experiment Conclusion

The crystalline form A of the compound of formula (I) has an increase in weight by moisture sorption of 1.789% at 25° C. and 80% RH, and thus is slightly hygroscopic.

Example 3: Biochemical Activity Assay for BRD4

Preparation of the Experiment 1) using BRD4-BD1 protein and BRD4-BD2 protein from BPS company for the experiments; as well as polypeptides from ANASPEC company; detection reagents from Perkinelmer company;
2) screening compounds by applying the experimental principle of TR-FRET;
3) testing the compounds.

The Experimental Steps are as Follows:

1) Preparation of Compound Plates

Preparation of Compound Plates in the Experiment was Achieved by Echo

The compound was diluted with Echo in 3-fold decreasing manner to 10 concentrations: 20000, 6666.67, 2222.22, 740.74, 246.91, 82.305, 27.435, 9.145, 3.048, 1.016 nM.

2) Preparation of Reaction Reagents

The Relevant Reagents should be Prepared on the Day of the Experiment:

a) preparing 1× assay buffer (test buffer solution);
b) preparing 3× solution of the experimental components:
1. The reagents were placed on ice, and spontaneously melt for later use
2. 1× assay buffer (test buffer solution) was used to prepare "solution A" (protein solution), "solution B" (polypeptide solution), and "solution C" (detection reagent solution) for the experiments, to allow the components in the reaction system to form 3× solutions, and the amount of solution A, B, C was sufficient for the required amount of the experiments.

3) The Experimental Operation Steps are as Follows

Assay plates were the plates containing compound gradient concentrations and corresponding DMSO solutions prepared before the experiment using ECHO:

a) taking out the assay plate, adding 5 µL/well of "solution A" (protein solution) into the columns 2-23 of the assay plate, and then adding 5 µL/well of 1× assay buffer into the columns 1 and 24 of the assay plate as Min control in the experimental system;
b) centrifuging at 1000 rpm for 30 seconds;
c) incubating the plate at 23° C. for 20 minutes;
d) adding 5 µL/well of "solution B" (polypeptide solution) to columns 1-24 of the assay plate after 20 minutes of incubation;

e) centrifuging at 1000 rpm for 30 seconds;
f) incubating the plate at 23° C. for 20 minutes;
g) adding 5 μL/well "solution C" (detection reagent solution) to columns 1-24 of the assay plate after 20 minutes of incubation;
h) centrifuging at 1000 rpm for 30 seconds;
i) incubating the plate at 23° C. for 40 minutes;
j) reading plates on an EnVision.

4) Data Analysis a) calculating the Z' value of each assay plate using corresponding Max control (maximum control) and Min control (minimum control) of each assay plate, and ensuring that the Z' value of each plate is greater than 0.5;
b) calculating $IC_{50}$ value from the signal for the test compounds by XLFIT5, and ensuring that it remains within 3-fold of the historical mean data, with the results as shown in Table 5.

TABLE 5

Test results of BRD4 test $IC_{50}$

| Compound | BRD4 (BD1, BD2), $IC_{50}$(nM) |
|---|---|
| Compounds of formula (I) | 66, 10 |

5) Conclusion

The compound of formula (I) has significant inhibitory effect on BRD4-BD1 and BRD4-BD2.

Example 4: In Vivo Pharmacodynamics Study of the Compound of Formula (I) in Human Breast Cancer MDA-MB-231_Luc Cell Subcutaneous Xenograft Tumor Model 1. Experiment Design

TABLE 6

Preparation method of substance to be tested

| Compound | Packaging or initial concentration | Formulation method | Concentration (mg/mL) | Storage conditions |
|---|---|---|---|---|
| Vehicle | — | 5% DMSO + 40% PEG400 + 10% Kolliphor ® HS 15 + 45% $H_2O$ | — | 4° C. |
| The compound of formula (I) 50 mg/kg, BID | 511 mg | 126.52 mg of the compound of formula (I) was added to a brown bottle, and then 1.26 mL of DMSO was added thereto. The mixture was mixed by vortex to a homogeneous solution. 10.080 mL of PEG400 and 2.52 mL of solutol were added and mixed by vortex until a homogeneous solution was formed, and then 11.340 mL of $H_2O$ was added and mixed by vortex to obtain a solution containing the compound of formula (I) at a concentration of 5 mg/mL. | 5 | 4° C. |

"BID": twice daily.

TABLE 7

Animal grouping and dosage regimen for in vivo pharmacodynamics experiments

| Group | Number of animals | Compound treatment | Dosage (mg/kg) | Administration volume parameter (μL/g) | Administration route | Administration frequency |
|---|---|---|---|---|---|---|
| 1 | 6 | Vehicle (Vehicle control group) | — | 10 | PO | BID × 21 days |
| 2 | 6 | Compound of formula (I) | 50 | 10 | PO | BID × 21 days |

"PO": administered orally by gavage.

2. Experiment Materials 2.1 Experiment Animals

Species: mouse
Strain: BALB/c nude mouse
Week-age and weight: 6-8 weeks of age, 18-22 grams of body weight
Sex: Female
Supplier: Shanghai Sippr-BK laboratory animal Co. Ltd.

3. Experiment Methods and Steps 3.1 Cell Culture

Human breast cancer MDA-MB-231_luc cells were cultured in monolayer in vitro and the culture conditions were RPMI-1640 culture medium (supplier: Gibco; article number: 22400-089; manufacturing batch number: 4868546) with 10% fetal bovine serum, 100 U/ml penicillin and 100 μg/mL streptomycin. The culture was performed at 37° C. in 5% $CO_2$. Conventional digestion treatment with pancreatin- EDTA for passage was carried out twice a week. When the cells were in the exponential growth phase, the cells were harvested, counted, and inoculated.

3.2 Tumor Cell Inoculation 0.2 mL of 10×10$^6$ MDA-MB-231_luc cells were subcutaneously inoculated into the right-back of each nude mouse (PBS:Matrigel=1:1). The grouping and administration was started when the average tumor volume reached 100-150 mm$^3$.

3.3 Tumor Measurement and Experiment Indices

The experiment index was to investigate whether tumor growth was inhibited, delayed or cured. Tumor diameter was measured twice a week with vernier calipers. The equation for calculating the tumor volume was V=0.5a×b$^2$, wherein a and b represented the major and minor diameters of the tumor, respectively.

The tumor inhibition effect of the compound was evaluated by TGI (%) or relative tumor proliferation rate T/C (%). TGI (%) reflected the tumor growth inhibition rate. Calculation of TGI (%) was as follows: TGI (%)=[(1−(average tumor volume at the end of administration in a treatment group−average tumor volume at the beginning of administration in this treatment group))/(average tumor volume at the end of treatment in the vehicle control group−average tumor volume at the beginning of treatment in the vehicle control group)]×100%.

Relative tumor proliferation rate T/C (%) was calculated according to the below equation: T/C %=$T_{RTV}$/$C_{RTV}$×100% ($T_{RTV}$: RTV of the treatment group; $C_{RTV}$: RTV of the negative control group). The relative tumor volume (RTV) was calculated according to the results of the tumor measurement. The calculation equation was RTV=$V_t$/$V_0$, where $V_0$ was the average tumor volume measured at the grouping and administration (i.e. d$_0$), and $V_t$ was the average tumor volume at the time of a certain measurement. $T_{RTV}$ and $C_{RTV}$ were obtained from the data on the same day.

At the end of the experiment, the tumor weight would be measured and the T/C$_{weight}$ percentage would be calculated. $T_{weight}$ and $C_{weight}$ represented the tumor weights of the administration group and the vehicle control group, respectively.

3.4 Statistical Analysis

Statistical analysis included mean value and standard error (SEM) of the tumor volume of each group at each time point. The treatment group showed the best treatment effect on the 21st day after the administration at the end of the experiment, so the statistical analysis was performed based on this data to evaluate the differences between the groups. The comparison between two groups was analyzed by T-test, and the comparison between three or more groups was analyzed by one-way ANOVA. If the F value was significantly different, the Games-Howell test was applied. If the F value was not significantly different, the Dunnet (2-sided) test was used for analysis. All data analysis was performed with SPSS 17.0. p<0.05 was considered significantly different.

4. Experiment Conclusion

On the 21st day after administration, for the compound of formula (I), the tumor growth inhibition rate TGI=54.85%, T/C=52.99%, p<0.05; there was no significant change in body weight of the animals, and they were well tolerated.

Example 5: In Vivo Pharmacodynamics Study of the Compound of Formula (I) in Human Prostatic Cancer PC-3 Cell Subcutaneous Xenograft Tumor Model

1. Experimental Design

The formulation method of the test substance was the same as in Table 6, and the animal grouping and the dosage regimen were the same as in Table 7.

2. Experiment Materials

2.1 Experiment Animals

Species: mouse

Strain: BALB/c nude mouse

Week-age and weight: 6-8 weeks of age, 18-22 grams of body weight

Sex: male

Supplier: Shanghai Sippr-BK laboratory animal Co. Ltd.

3. Experiment Methods and Steps

3.1 Cell Culture

Human prostatic cancer PC-3 cells were cultured in monolayer in vitro, and the culture conditions were F-12K culture medium (supplier: Gibco; article number: 21127-022; manufacturing batch number: 1868870) with 10% fetal bovine serum, 100 U/mL penicillin and 100 µg/mL streptomycin. The culture was performed at 37° C. in 5% $CO_2$. Conventional digestion treatment with pancreatin-EDTA for passage was carried out twice a week. When the cells were in the exponential growth phase, the cells were harvested, counted, and inoculated.

3.2 Tumor Cell Inoculation 0.1 mL of 10×10$^6$ PC-3 cells were subcutaneously inoculated into the right-back of each nude mouse. The grouping and administration was started when the average tumor volume reached 100-150 mm$^3$.

3.3 Tumor measurement, experiment indices, and statistical analysis were the same as MDA-MB-231 model.

4. Experiment Conclusion

On the 21st day after administration, compared with the vehicle control group, the test compound of formula (I) had a significant tumor inhibition effect (T/C=44.63%, TGI=58.4%, p=0.033); the animals were well tolerated.

Example 6: In Vivo Anti-Tumor Effect of the Compound of Formula (I) in MC38 Mouse Colon Cancer Cell Animal Transplantation Tumor Model 1. Experiment Design

| Group | Number of animals | Substance tested | Dosage mg/kg | Administration volume mL/kg | Administration route | Administration frequency and cycle |
|---|---|---|---|---|---|---|
| 1 | 10 | Vehicle control group | — | 10 | PO | BID × 20 days |
| 2 | 10 | Compound of formula (I) | 15 | 10 | PO | BID × 20 days |
| 3 | 10 | Compound of formula (I) | 25 | 10 | PO | BID × 20 days |
| 4 | 10 | Compound of formula (I) | 50 | 10 | PO | BID × 20 days |

2. Experiment Material 2.1 Experiment Animals

Species: mouse
Strain: C57BL6 mouse
Week-age and weight: 6-7 weeks of age, 16-20 grams of body weight
Sex: Female
Supplier: Shanghai SLAC Laboratory Animal Co., Ltd.

3. Experiment Methods and Steps 3.1 Cell Culture

Mouse colon cancer MC38 cells (OBiO Technology (Shanghai) Corp., Ltd.) were cultured in monolayer in vitro, and the culture conditions were DMEM culture medium (Gibco; article number: 12100) with 10% fetal bovine serum at 37° C. in 5% $CO_2$ in an incubator. Conventional digestion treatment with 0.25% pancreatin-EDTA for passage was carried out. When the cells were in the exponential growth phase and the density was 80%-90%, the cells were harvested, counted, and inoculated.

3.2 Tumor Cell Inoculation 0.1 mL of $2 \times 10^5$ MC38 cells were subcutaneously inoculated into the right-back of each mouse. The random grouping and administration was carried out according to the tumor volume when the average tumor volume reached about 70 mm³.

3.3 Tumor Measurement

Tumor diameter was measured twice a week with vernier calipers. The equation for calculating tumor volume was $V = 0.5 \times a \times b^2$, wherein a and b represented the major and minor diameters of the tumor, respectively.

The tumor inhibition effect of the compound was evaluated by TGI (%) or relative tumor proliferation rate T/C (%). Relative tumor proliferation rate T/C (%) = $T_{RTV}/C_{RTV} \times 100\%$ ($T_{RTV}$: RTV of the treatment group; $C_{RTV}$: RTV of the negative control group). The relative tumor volume (RTV) was calculated according to the results of the tumor measurement. The calculation equation was RTV = $V_t/V_0$, where $V_0$ was the average tumor volume measured at the grouping and administration (i.e. D0), and $V_t$ was the average tumor volume at the time of a certain measurement. $T_{RTV}$ and $C_{RTV}$ were obtained from the data on the same day.

TGI (%) reflected the tumor growth inhibition rate. TGI (%) = [(1−(average tumor volume at the end of administration in a treatment group−average tumor volume at the beginning of administration in this treatment group))/(average tumor volume at the end of treatment in the vehicle control group−average tumor volume at the beginning of treatment in the vehicle control group)] × 100%.

At the end of the experiment, the tumor weight would be measured and the $T_{weight}/C_{weight}$ percentage would be calculated. $T_{weight}$ and $C_{weight}$ represented the tumor weights of the administration group and the vehicle control group, respectively.

3.4 Statistical Analysis

Statistical analysis was performed using SPSS software based on the tumor volume and the tumor weight at the end of the experiment. The comparison between two groups was analyzed by t-test, and the comparison between three or more groups was analyzed by one-way ANOVA. If the variance was homogeneous (the F value was not significantly different), the LSD method was used for analysis. If the variance was not homogeneous (the F value was significantly different), the Games-Howell method was used for the test. $p < 0.05$ was considered significantly different.

4. Experiment Conclusion

On the 20th day after administration, for the test compound of formula (I), for the 15 mg/kg administration group: the relative tumor proliferation rate T/C = 33.68%, the tumor growth inhibition rate TGI = 68.81%, $p < 0.0001$; for the 25 mg/kg administration group: the relative tumor proliferation rate T/C = 27.59%, TGI = 75.21%, $p < 0.0001$; and for the 50 mg/kg administration group: T/C = 10.04%, TGI = 93.46%, $p < 0.0001$. Significant tumor inhibition effects were shown in each administration group of animals with good tolerance.

Example 7 In Vivo Pharmacokinetics Test of the Compound of Formula (I) in Mice

Female Balb/c mice were used as test animals. The compound of formula (I) was administrated intravenously and intragastrically to mice, then the drug concentrations in the plasma at different time points were determined by the LC/MS/MS method. The in vivo pharmacokinetic behavior of the compound of formula (I) in mice was studied, and its pharmacokinetic characteristics were evaluated.

1. Experiment Protocol 1.1 Experiment Drug: The Compound of Formula (I)

1.2 Experiment Animals

Sixteen healthy adult female Balb/c mice were divided into four groups according to the principle of similar body weight, with four mice in each group. The animals were purchased from Shanghai Lingchang BioTech Co., Ltd. of Shanghai SLAC Laboratory Animal Co., Ltd., and the animal production license number was SCXK (Shanghai) 2013-0018.

1.3 Drug Formulation

An appropriate amount of the sample was taken, 5% final volume of DMSO was added, and then 95% final volume of 20% HP-β-CD was added. The mixture was ultrasonically stirred to obtain a 0.5 mg/mL clear solution. After filtration, it was used for the intravenous administration.

An appropriate amount of the sample was taken, and dissolved in a 0.5% sodium carboxymethyl cellulose solution. The mixture was ultrasonically stirred to obtain a 0.5 mg/mL homogeneous suspension, which was used for the intragastric administration.

1.4 Administration

Eight female Balb/c mice were divided into two groups. After fasting overnight, the first group was administered intravenously with the administration volume of 2.5 mL/kg and the dosage of 1 mg/kg. The second group was administered intragastrically with the administration volume of 5 mL/kg and the dosage of 3 mg/kg.

2. Operation

After the female Balb/c mice were intravenously administrated, 30 μL of blood was taken at each time point of 0.0833, 0.25, 0.5, 1, 2, 4, 8 and 24 hours, and placed in test tubes containing 2 μL of EDTA-$K_2$; and after the female Balb/c mice were intragastrically administrated, 30 μL of blood was taken at each time point of 0.0833, 0.25, 0.5, 1, 2, 4, 8 and 24 hours, and placed in test tubes containing 2 μL of EDTA-$K_2$. The tube was centrifuged at 3000 g for 15 minutes to separate the plasma, and the separated plasma was stored at −60° C. Animals could be fed 2 hours after the administration.

The LC/MS/MS method was used to measure the content of the compound to be tested in the plasma after the intravenous and intragastric administration to the mice. The linear range of the method was 2.00-6000 nmol/L; the plasma samples were analyzed after the protein precipitation by acetonitrile treatment. The results of the pharmacokinetic parameters were shown in Table 8.

Experiment conclusion: the compound of formula (I) has high exposure by oral administration, low drug clearance rate and high oral bioavailability.

Example 8 In Vivo Pharmacokinetics Test of the Compound of Formula (I) in Rat Male SD rats were used as test animals. The compound of formula (I) was administrated intravenously and intragastrically to rats, and then the drug concentrations in the plasma at different time points were determined by the LC/MS/MS method. The in vivo pharmacokinetic behavior of the compound of formula (I) in rats was studied, and its pharmacokinetic characteristics were evaluated.

1. Experiment Protocol

1.1 Experiment Drug: The Compound of Formula (I) (the Crystalline Form A)

1.2 Experiment Animals 4 healthy adult male SD rats were divided into 2 groups according to the similar weight principle, with 2 rats in each group. The animals were commercially available from Beijing Weitonglihua Laboratory Animals Ltd., animal production license number: SCXK (Beijing) 2016-0006.

1.3 Drug Formulation

An appropriate amount of the sample was taken, 5% final volume of DMSO was added, and then 95% final volume of 20% HP-β-CD was added. The mixture was ultrasonically stirred to obtain a 0.5 mg/mL clear solution. After filtration, it was used for the intravenous administration.

An appropriate amount of the sample was taken, and dissolved in a 0.5% sodium carboxymethyl cellulose solution. The mixture was ultrasonically stirred to obtain a 1 mg/mL homogeneous suspension, which was used for the intragastric administration.

1.4 Administration

Four male SD rats were divided into two groups. After fasting overnight, the first group was administered intravenously with the administration volume of 4 mL/kg and the

TABLE 8

The results of the pharmacokinetic parameters

| Compound | Administration mode | Administration dosage | Drug concentration in blood $C_{max}$ (nM) | Time to peak $T_{max}$ (h) | Half life $T_{1/2}$ (h) | Apparent distribution volume $V_{dss}$ (L/kg) | Clearance rate Cl (mL/min/kg) | Area under curve (0-t) $AUC_{0-last}$ (nM·h) | Area under curve (0-inf) $AUC_{0-inf}$ (nM·h) | Bioavailability F (%) |
|---|---|---|---|---|---|---|---|---|---|---|
| Compound of formula (I) | Intravenous administration | 1 mg/kg | — | — | 1.09 | 1.19 | 12.5 | 2490 | 2502 | — |
| | Intragastric administration | 3 mg/kg | 930 | 1.00 | 1.47 | — | — | 2740 | 2818 | 37.5% |

"—": Not applicable.

dosage of 2 mg/kg. The second group was administered intragastrically with the administration volume of 10 mL/kg and the dosage of 10 mg/kg.

2. Operation

After the male SD rats were intravenously administered, 100 μL of blood was taken at each time point of 0.0833, 0.25, 0.5, 1, 2, 4, 6, 8 and 24 hours, and placed in test tubes containing 2 μL of EDTA-$K_2$; and after the SD rats were intragastrically administered, 100 μL of blood was taken at each time point of 0.0833, 0.25, 0.5, 1, 2, 4, 6, 8 and 24 hours, and placed in test tubes containing 2 μL of EDTA-$K_2$. The tube was centrifuged at 3000 g for 15 minutes to separate the plasma, and the separated plasma was stored at −60° C. Animals could be fed 2 hours after the administration.

The LC/MS/MS method was used to measure the content of the compound to be tested in the plasma after the intravenous and intragastric administration to the rats. The linear range of the method was 2.00-6000 nmol/L; the plasma samples were analyzed after the protein precipitation by acetonitrile treatment. The results of the pharmacokinetic parameters were shown in Table 9.

centrifuged. The supernatant was removed, and then 5 mL of culture medium was added for resuspension to ensure that the cell density was 2-5×$10^6$/mL.

1.4 Solution Preparation

The method for preparing the solution is shown in Table 10 below.

TABLE 10

| | Composition of intracellular and extracellular fluids | |
|---|---|---|
| Reagent | Extracellular fluid (mM) | Intracellular fluid (mM) |
| $CaCl_2$ | 2 | 5.374 |
| $MgCl_2$ | 1 | 1.75 |
| KCl | 4 | 120 |
| NaCl | 145 | — |
| Glucose | 10 | — |
| HEPES | 10 | 10 |

TABLE 9

| | | | The results of the pharmacokinetic parameters | | | | | | |
|---|---|---|---|---|---|---|---|---|---|
| Compound | Administration mode | Administration dosage | Drug concentration in blood $C_{max}$ (nM) | Time to peak $T_{max}$ (h) | Half life $T_{1/2}$ (h) | Apparent distribution $V_{dss}$ (L/kg) | Clearance rate Cl (mL/min/kg) | Area under curve (0-t) $AUC_{0-last}$ (nM · h) | Area under curve (0-inf) $AUC_{0-inf}$ (nM · h) | Bioavailability Bioavailability (%) |
| Compound of formula (I) | Intravenous administration | 2 mg/kg | — | — | 0.683 | 1.48 | 28.3 | 2212 | 2216 | — |
| | Intragastric administration | 10 mg/kg | 1165 | 1.00 | 1.01 | — | — | 3219 | 3248 | 29.3% |

"—": Not applicable.

Experiment conclusion: the compound of formula (I) has high exposure by oral administration, low drug clearance rate and high oral bioavailability.

Example 9: Assay of the Effect of the Compound of Formula (I) on hERG Potassium Ion Channel The effect of the compound of formula (I) on the hERG potassium channel current was investigated by adopting CHO (Chinese Hamster ovary) cell stably expressing the hERG potassium ion channel and using the fully automatic patch-clamp QPatch technology.

1. Experiment Protocol

1.1 Experiment Drug: the Compound of Formula (I)

1.2 Experiment System: CHO-hERG Cell Line

1.3 Preparation of Cells

CHO-hERG cells were cultured in a 175 $cm^2$ culture flask. After the cell density increased to 60-80%, the culture medium was removed, the cells were washed once with 7 mL PBS, and then 3 mL Detachin was added for digestion.

After the digestion was complete, 7 mL of culture medium was added for neutralization, and then the mixture was TABLE 10-continued

| | Composition of intracellular and extracellular fluids | |
|---|---|---|
| Reagent | Extracellular fluid (mM) | Intracellular fluid (mM) |
| EGTA | — | 5 |
| Na-ATP | — | 4 |
| pH | 7.40 (adjusted by NaOH), osmotic pressure ~305 mOsm | 7.25 (adjusted by KOH), osmotic pressure ~290 mOsm |

2. Operation 20 mM Stock solution of the compound was diluted with extracellular fluid, and 5 μL of 20 mM stock solution of the compound was added to 2495 μL of the extracellular fluid, diluted to 40 μM by 500-fold dilution, and then subjected to a 3-fold serial dilution successively with extracellular fluid containing 0.2% DMSO to obtain the required final concentration to be tested. The highest test concentration was 40 μM, which were in turn 40, 13.33, 4.44, 1.48, 0.49, 0.16 μM respectively, a total of 6 concentrations. The final concentration of DMSO in the test does not exceed 0.2%, which has no effect on hERG potassium channel.

The single-cell high-impedance sealing and the whole-cell mode formation process were all automatically completed by the Qpatch instrument. After the whole-cell recording mode was obtained, the cells were clamped at −80 millivolts. The cells first underwent a pre-voltage of −50 millivolts for 50 milliseconds, then underwent depolarization stimulation at +40 millivolts for 5 seconds, then underwent repolarization at −50 millivolts for 5 seconds, and then the voltage returned to −80 millivolts. This voltage stimulation was applied every 15 seconds. The data were recorded for 2 minutes, then extracellular fluid was given, and then the data were recorded for 5 minutes. Then, the administration of drug began. The concentration of the test compound started from the lowest concentration, each test concentration was tested for 2.5 minutes. After all the concentrations were administered continuously, 3 µM of Cisapride was administrated as the positive control compound. At least three cells (n≥3) were tested at each concentration. The experimental data were analyzed by XLFit software.

3. Conclusion

The results show that the compound of formula (I) inhibits hERG potassium current with $IC_{50}>40$ µM.

The invention claimed is:

1. A compound of formula (I) in crystal form,

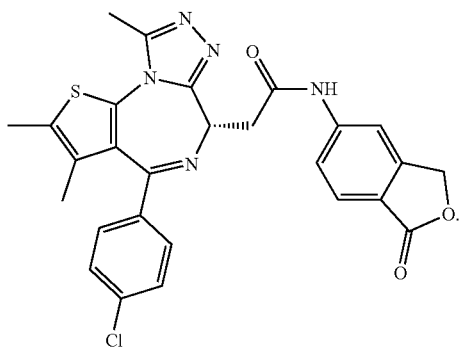

(I)

2. The compound of formula (I) in crystal form according to claim 1, which is a crystalline form A of the compound of formula (I), wherein an X-ray powder diffraction pattern of the crystalline form A comprises characteristic diffraction peaks at the following 2θ angles: 7.03±0.2°, 11.28±0.2°, 14.00±0.2°.

3. The compound of formula (I) in crystal form according to claim 2, wherein a differential scanning calorimetry curve of the crystalline form A comprises an onset of an endothermic peak at 289.22±3° C., and/or a thermal gravimetric analysis pattern of the crystalline form A shows a weight loss of 1.626% at 300.00±3° C.

Figure 2:
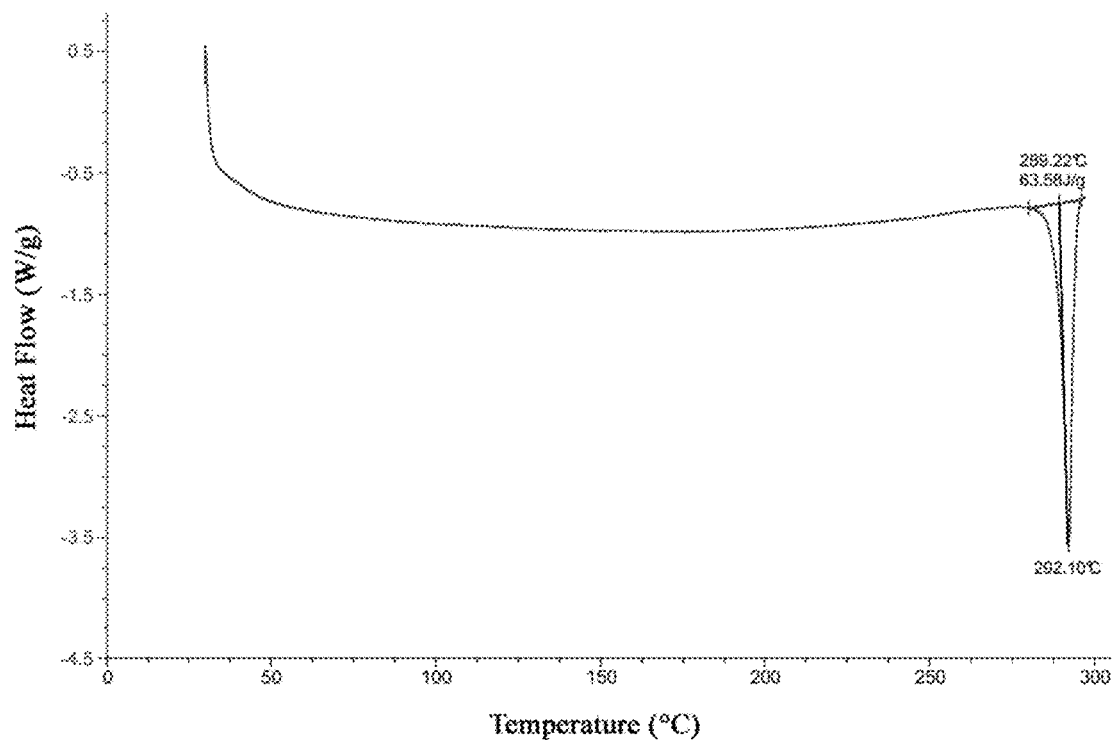
FIG. 2 is a DSC curve of the crystalline form A of the compound of formula (I).
Figure 3:
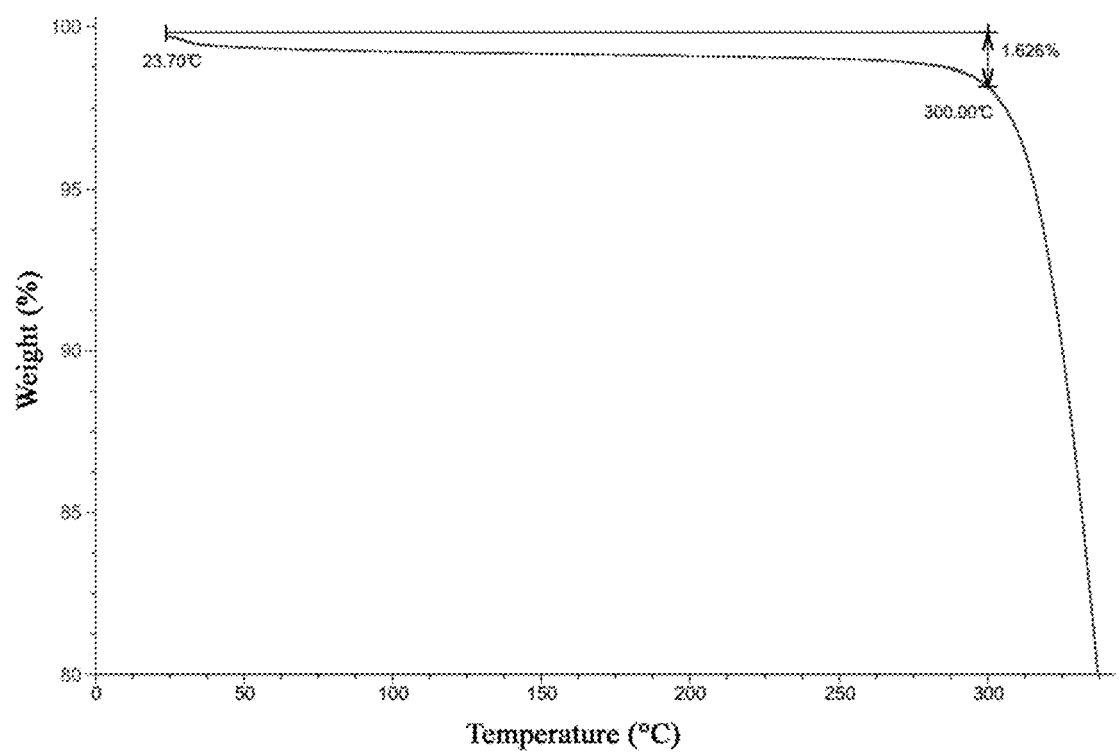
FIG. 3 is a TGA pattern of the crystalline form A of the compound of formula (I).

4. The compound of formula (I) in crystal form according to claim 3, wherein a DSC curve of the crystalline form A is substantially as shown in FIG. 2, and/or a TGA pattern of the crystalline form A is substantially as shown in FIG. 3.

5. The compound of formula (I) in crystal form according to claim 1, which is a crystalline form B of the compound of formula (I), wherein an X-ray powder diffraction pattern of the crystalline form B comprises characteristic diffraction peaks at the following 2θ angles: 5.50±0.2°, 8.36±0.2°, 11.87±0.2°.

6. A method for the preparation of the compound of formula (I) in crystal form according to claim 2, comprising:

(1) adding the compound of formula (I) into a solvent to form a suspension or a solution;
wherein the solvent is selected from the group consisting of methyl tert-butyl ether, ethyl acetate, acetonitrile, ethanol, acetone, methanol, methyl ethyl ketone, a mixed solvent of acetone-water with a volume ratio of 2:1, and a mixed solvent of ethanol-water with a volume ratio of 3:1, (2) stirring the suspension or the solution in a constant-temperature thermomixer at 25-45° C., then separating, and drying to obtain the crystalline form A of the compound of formula (I); and optionally, wherein the separation in step (2) is centrifugation or filtration.

7. A process for preparing the compound of formula (I) in crystal form according to claim 5, comprising:

(1) adding the compound of formula (I) into tetrahydrofuran to form a suspension or a solution;

(2) stirring the suspension or the solution in a constant-temperature thermomixer at 25-45° C., then separating, and drying to obtain the crystalline form B of the compound of formula (I); and optionally, wherein the separation in step (2) is centrifugation or filtration.

8. A pharmaceutical composition comprising the compound of formula (I) in crystal form according to claim 1.

9. A method for treating diseases selected from the group consisting of hematological tumors and advanced solid tumors, comprising administering the compound of formula (I) in crystal form according to claim 1 to a subject in need thereof.

10. A method for treating BRD4-related diseases, comprising administering the compound of formula (I) in crystal form according to claim 1 to a subject in need thereof.

11. A method in vivo or in vitro for inhibiting BRD4 protein activity, comprising contacting an effective amount of the compound of formula (I) in crystal form according to claim 1 with the BRD4 protein.

12. The compound of formula (I) in crystal form according to claim 1, which is a crystalline form A of the compound of formula (I), wherein an X-ray powder diffraction pattern of the crystalline form A comprises characteristic diffraction peaks at the following 2θ angles: 7.03±0.2°, 11.28±0.2°, 20.07±0.2°;

or an X-ray powder diffraction pattern of the crystalline form A comprises characteristic diffraction peaks at the following 2θ angles: 7.03±0.2°, 19.48±0.2°, 20.07±0.2°, 26.05±0.2°;

or an X-ray powder diffraction pattern of the crystalline form A comprises characteristic diffraction peaks at the following 2θ angles: 7.03±0.2°, 11.28±0.2°, 19.48±0.2°, 20.07±0.2°, 26.05±0.2°;

or an X-ray powder diffraction pattern of the crystalline form A comprises characteristic diffraction peaks at the following 2θ angles: 7.03±0.2°, 11.28±0.2°, 17.31±0.2°, 19.48±0.2°, 20.07±0.2°, 26.05±0.2°.

13. The compound of formula (I) in crystal form according to claim 1, which is a crystalline form A of the compound of formula (I), wherein an X-ray powder diffraction pattern of the crystalline form A comprises characteristic diffraction peaks at the following 2θ angles: 7.03±0.2°, 11.28±0.2°, 14.00±0.2°, 15.11±0.2°, 17.31±0.2°, 19.48±0.2°, 20.07±0.2°, 26.05±0.2°;

or an X-ray powder diffraction pattern of the crystalline form A comprises characteristic diffraction peaks at the following 2θ angles: 7.03±0.2°, 11.28±0.2°, 12.39±0.2°, 14.00±0.2°, 15.11±0.2°, 17.31±0.2°, 19.48±0.2°, 20.07±0.2°, 22.86±0.2°, 26.05±0.2°;
or an XRPD pattern of the crystalline form A is substantially as shown in FIG. 1.

Figure 4:
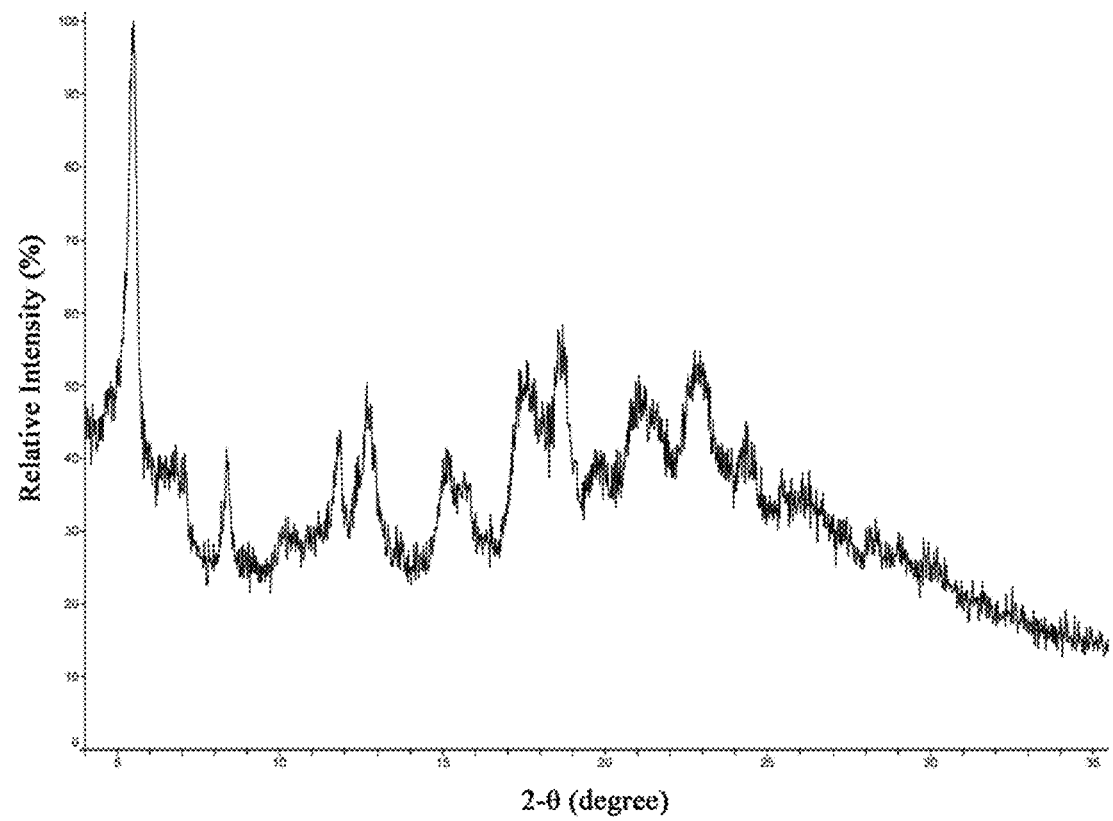
FIG. 4 is an XRPD pattern of Cu-Kα radiation of the crystalline form B of the compound of formula (I).

14. The compound of formula (I) in crystal form according to claim 1, which is a crystalline form B of the compound of formula (I), wherein an X-ray powder diffraction pattern of the crystalline form B comprises characteristic diffraction peaks at the following angles 2θ:5.50±0.2°, 8.36±0.2°, 12.66±0.2°;
or an X-ray powder diffraction pattern of the crystalline form B comprises characteristic diffraction peaks at the following angles 2θ:5.50±0.2°, 8.36±0.2°, 11.87±0.2°, 12.39±0.2°, 12.66±0.2°, 15.11±0.2°, 17.35±0.2°, 18.70±0.2°;
or an XRPD pattern of the crystalline form B is substantially as shown in FIG. 4.

15. A method according to claim 9, wherein the hematological tumors comprise leukemia, acute lymphoblastic leukemia, lymphoma, acute myeloid lymphoma and myeloma; and the advance solid tumors comprise neurocytoma, glioma, breast cancer, triple negative breast cancer, gastrointestinal tumor, colorectal cancer, and prostate cancer.

\* \* \* \* \*